(12) United States Patent
Hengerer

(10) Patent No.: US 12,402,956 B2
(45) Date of Patent: Sep. 2, 2025

(54) APPARATUS AND METHOD FOR GUIDING AN INSTRUMENT BY A LUMINOUS POINTER

(71) Applicant: Siemens Healthcare GmbH, Erlangen (DE)

(72) Inventor: Arne Hengerer, Möhrendorf (DE)

(73) Assignee: Siemens Healthineers AG, Forchheim (DE)

( * ) Notice: Subject to any disclaimer, the term of this patent is extended or adjusted under 35 U.S.C. 154(b) by 221 days.

(21) Appl. No.: 18/083,797

(22) Filed: Dec. 19, 2022

(65) Prior Publication Data
US 2023/0200912 A1 Jun. 29, 2023

(30) Foreign Application Priority Data
Dec. 27, 2021 (EP) ..................... 21217857

(51) Int. Cl.
*A61B 34/20* (2016.01)
*A61B 5/055* (2006.01)
(Continued)

(52) U.S. Cl.
CPC ............ *A61B 34/20* (2016.02); *A61B 5/055* (2013.01); *A61B 10/0233* (2013.01);
(Continued)

(58) Field of Classification Search
None
See application file for complete search history.

(56) References Cited

U.S. PATENT DOCUMENTS

| 2008/0194945 A1* | 8/2008 | Kukuk | A61B 6/463 |
| | | | 600/424 |
| 2015/0085261 A1 | 3/2015 | Lee | |

(Continued)

FOREIGN PATENT DOCUMENTS

EP    3779493 A1    2/2021

OTHER PUBLICATIONS

Sasa Mutic, CT Laser Guidance; download: "Microsoft PowerPoint—26-4439-90304-675.ppt (aapm.org)"; Aug. 15, 2006. pp. 1-17.

*Primary Examiner* — Ashley K Buran
*Assistant Examiner* — Tommy T Ly
(74) *Attorney, Agent, or Firm* — Lempia Summerfield Katz LLC

(57) ABSTRACT

An instrument, a magnetic resonance imaging scanner and a method for operating the magnetic resonance imaging scanner with the instrument in which the instrument is aligned with a patient. The medical instrument comprises a first projector for projecting a luminous pointer in a predetermined alignment relative to the medical instrument. The magnetic resonance imaging scanner comprises a positioning aid configured to mark a predetermined position on an inner wall of a patient tunnel in a manner that is visible to a user. In the method, a predetermined alignment of the first projector relative to the medical instrument or position of the positioning aid on the wall of the patient tunnel is ascertained in which the luminous pointer of the first projector coincides with the positioning aid when the medical instrument is aligned parallel to a trajectory through an entry point on the patient and a target point in the patient and the medical instrument is aligned such that the luminous pointer and the positioning aid coincide.

5 Claims, 5 Drawing Sheets

(51) Int. Cl.
*A61B 10/02* (2006.01)
*A61B 17/34* (2006.01)
*A61B 90/00* (2016.01)

(52) U.S. Cl.
CPC .. *A61B 17/3403* (2013.01); *A61B 2034/2055* (2016.02); *A61B 2090/3937* (2016.02)

(56) References Cited

U.S. PATENT DOCUMENTS

| | | |
|---|---|---|
| 2015/0196367 A1* | 7/2015 | Muller .................. A61B 6/54 600/410 |
| 2016/0000516 A1 | 1/2016 | Cheng et al. |
| 2022/0291308 A1 | 9/2022 | Leussler et al. |

\* cited by examiner

APPARATUS AND METHOD FOR GUIDING AN INSTRUMENT BY A LUMINOUS POINTER

CROSS REFERENCE TO RELATED APPLICATIONS

This application claims the benefit of EP21217857.8, filed on Dec. 27, 2021, which is hereby incorporated by reference in its entirety.

FIELD

Embodiments relate to an instrument, a magnetic resonance imaging scanner and a method for operating the magnetic resonance imaging scanner with the instrument in which the instrument is aligned with a patient.

BACKGROUND

Magnetic resonance imaging scanners are imaging apparatuses that, to map an object under examination, align nuclear spins of the object under examination with a strong external magnetic field and excite them to precess about this alignment by an alternating magnetic field. The precession or return of the spins from this excited state to a lower energy state in turn creates an alternating magnetic field in response which is received via antennas.

Magnetic gradient fields are used to impart spatial encoding to the signals that subsequently provides the assignment of the received signal to a volume element. The received signal is then evaluated and a three-dimensional imaging representation of the object under examination is provided. The signal may be received using local receiving antennas, so-called local coils, that are arranged directly on the object under examination in order to achieve a better signal-to-noise ratio.

A magnetic resonance imaging scanner provides visualization of the interior of the body over a longer period without exposing the patient or surgeon to an increased dose of ionizing radiation. However, instruments made of plastic or metal cannot be detected, or may only be detected indirectly, by magnetic resonance imaging and thus alignment is difficult.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a method and an apparatus that provide for an instrument to be positioned and aligned with little additional effort.

The medical instrument is intended for use on or in a patient. The instrument may, for example, be a biopsy needle, an instrument for ablation or for applying brachytherapy.

The medical instrument includes a first projector for projecting a luminous pointer in a predetermined alignment relative to the medical instrument. A luminous pointer is considered to be a light pattern created by the projector on an inner surface of a patient tunnel that provides the projector, and thus the instrument, to be aligned with an angular error of less than 5 degrees, 2 degrees or 1 degree.

According to the embodiments described below, the projector may, for example, be a simple light source with an optical system for alignment into a parallel beam, a laser with a collimation optical system, or also a projector that illuminates a pattern with a light source and projects it onto the inner wall. Variable projection by technology comparable to a beamer or by projection of an OLED matrix with an optical system may also be used.

With the instrument, when the medical instrument is positioned on the patient appropriately for the application, the predetermined alignment of the first projector is directed away from the patient. In other words, when the medical instrument is arranged appropriately for the application, the luminous pointer of the projector does not strike the patient, but strikes the surrounding inner wall of the patient tunnel.

The projector provides a second reference point for the alignment of the medical instrument to be created on the wall of the patient tunnel and used in addition to the contact point or entry point on the patient.

The magnetic resonance imaging scanner includes a positioning aid. The positioning aid is configured to mark a predetermined position on an inner wall of a patient tunnel in a manner that is visible to a user. In other words, the positioning aid provides a user to identify a location on the inner wall of the tunnel, for example as a target for the light pointer of the first projector of the medical instrument. The positioning aid may, for example, be a single marking that differs in reflectivity from the surrounding inner wall. An elevation or depression on the surface of the inner wall may be used. However, temporary markings, which may be rendered visible variably by the magnetic resonance imaging scanner may be used.

The positioning aids interact with the instrument to provide a defined alignment of the instrument.

The method relates to the positioning of an above-described medical instrument with a first projector for projecting a luminous pointer and a magnetic resonance imaging scanner with a positioning aid. The method is furthermore executed with a planning controller with an operator interface for planning an intervention with the medical instrument. Herein, the planning controller may be executed as a program on the magnetic resonance imaging scanner and use its output or also be executed on another computer or in a cloud as a separate unit.

In one step of the method the patient is positioned in the magnetic resonance imaging scanner. This is done in such a way that a predetermined entry point for the medical instrument on the surface of the patient and a predetermined target point of the intervention in the patient are located in a detection area of the magnetic resonance imaging scanner. The detection area is also referred to as the field of view (FoV). Positioning may take place by the patient couch. The entry point may, for example, be marked with a magnetic resonance-active marker.

In a further step of the method a predetermined alignment of the first projector relative to the medical instrument and/or position of the positioning aid on the wall of the patient tunnel is ascertained in which the luminous pointer of the first projector coincides with the positioning aid when the medical instrument is aligned parallel to a trajectory through the entry point and the target point. The idea is to achieve the alignment of the instrument in that a user aligns the luminous pointer with the positioning aid as explained in the following step. Either the position of the positioning aid to be targeted with the luminous pointer is changed in order to support or determine a changed alignment or the alignment of the first projector relative to the medical instrument is changed. Accordingly, in this step, the position of the positioning aid or the alignment of the first projector relative to the instrument under which the medical instrument is aligned parallel to the trajectory when the luminous pointer hits the positioning aid is determined. The calculation takes place in accordance with analytical geometry in the controller of the magnetic resonance imaging scanner, planning controller, or another computer by using rotations and determining a point of intersection of a straight line with a surface of the patient tunnel. The two parameters, position of the positioning aid, and alignment of the first projector, may be changed simultaneously and ascertained accordingly.

In another step of the method the first projector is brought into the ascertained relative alignment with the medical instrument. This may, for example, take place by actuators on the projector that are connected to the controller of the magnetic resonance imaging scanner, for example via a wireless signal connection.

Supplementarily or alternatively, the positioning aid is output. In the simplest case, this may entail outputting coordinates for the user on an output. Herein, the coordinates relate to a coordinate system that is attached in a visible manner to the inside of the patient tunnel and indicates a clear target position for the luminous pointer as a positioning aid for the user on the basis of the coordinates. However, a positioning aid that, for example, indicates a grid of light spots from which the light spot closest to the position of the luminous pointer to be achieved is activated may be used. For better compatibility with the magnetic resonance imaging scanner, the light spots may also be implemented by glass fibers with the light source being arranged away from the patient tunnel. A projection of the positioning aid would also be possible. The luminous pointer is activated if it is not already active.

The method provides the user to be provided with a simple and reliable aid for the alignment of the medical instrument.

In an embodiment of the medical instrument the medical instrument includes an axis of symmetry. The axis of symmetry may be a mirror-symmetrical axis or, for example, an axis for rotational symmetry.

Aligning the first projector parallel to an axis of symmetry, for example an axis of rotation, provides the medical instrument to be held in different rotational positions without thereby changing the alignment. In the case with rotationally symmetrical instruments, such as a biopsy needle, this simplifies alignment.

In an embodiment of the medical instrument, the instrument includes a control input and is configured to change the predetermined alignment of the first projector in a predetermined manner in dependence on an instruction via the control input. Herein, alignment of the projector may be understood as the alignment of the projection of the luminous pointer with respect to the medical instrument. The first projector may be aligned mechanically relative to the instrument by actuators based on the instruction. However, the projector may also be configured to change the alignment of the luminous pointer, for example in that the projector relies on an image being projected with the luminous pointer and this image being changed in that the position of the luminous pointer is changed within the image. This may, for example, be achieved by projecting an OLED, DLP or LCD matrix. The control input may, for example, be an electrical or optical signal line or also a wireless data transmission, for example by Bluetooth or WLAN.

If the alignment of the first projector is variable, one single positioning aid, or at least a small number of positioning aids, on the inner wall of the patient tunnel may be sufficient to ensure precise alignment.

In an embodiment of the medical instrument, the instrument includes a sensor configured to detect an alignment of the instrument about the axis of symmetry relative to the magnetic resonance imaging scanner. For example, a sensor that ascertains the direction of gravity or of the B0 magnetic field.

When the first projector is aligned relative to the instrument, the instrument may still be rotated by the user. If rotation about the axis of symmetry is determined by the sensor, the alignment of the first projector may be set in order to align the luminous pointer correctly taking account of the rotation.

The luminous pointer and the positioning aid may be configured to identify, for example by a pattern and/or a shape of the luminous pointer, a rotation of the instrument about the axis of symmetry. In conjunction with a position marking, this may simultaneously indicate the alignment of the trajectory and rotation about the axis of symmetry and the user may thus set the alignment correctly. For example, the luminous pointer and positioning aid may include a directional arrow with a dot or circle at the origin. When the user causes the origin marking and the arrow to coincide, this provides the instrument to be aligned even if the axis of rotation of the instrument is different from the direction of projection of the first projector.

In an embodiment of the magnetic resonance imaging scanner the positioning aid includes a marking attached in a visible manner to the inside of the patient tunnel. Positioning aids are markings that are different in color or reflection behavior or depressions or elevations that differ in shape from the surface. The positioning aid may also include a coordinate system on the inner wall of the patient tunnel.

A visible positioning aid is advantageously simple to attach and use.

In an embodiment of the magnetic resonance imaging scanner the magnetic resonance imaging scanner includes a second projector. The second projector is configured to mark a predetermined position on the inner wall of the patient tunnel in a visible manner by a light projection as a positioning aid. As described above with respect to the first projector, the second projector may be a laser or pointer that casts a single light spot onto the inner wall, or also a symbol or an entire pattern, such as a coordinate system. The second projector may be suitable for marking different positions, for example by projecting a pattern at different positions. This may, for example, be achieved in that the alignment of the second projector may be changed by the planning controller, or different images may be projected with the symbol or pattern at different positions.

The second projector provides variable positions to be marked on the inner wall of the patient tunnel in order to achieve different alignments with a medical instrument.

In an embodiment, the method further includes the step of aligning the medical instrument such that the luminous pointer coincides with the positioning aid. The user of the medical instrument places the end or tip of the medical instrument that is opposite to the direction of projection of the first projector at the predetermined entry point. The entry point may be marked with an MR-active marker. The user then tilts and swivels the medical instrument such that the luminous pointer and the positioning aid are caused to coincide. If the luminous pointer and the positioning aid are not configured as rotationally symmetrical, but have a preferred direction to indicate rotation of the instrument about the trajectory, the luminous pointer and the positioning aid are aligned with one another as predetermined in order to achieve the desired orientation. For example, as described above, pointers may be caused to coincide.

Alignment by the luminous pointer is a simple way of ensuring the desired alignment of the medical instrument with the target point.

In an embodiment, the method furthermore includes the steps of providing a map of a patient on the operator interface of the planning controller and using the map to define an entry point on the surface of the patient and a target point in the patient by the user. The entry point in the map may be made visible by an MR active marker or made visible by deformation of the surface by the instrument or another object, such as, for example, a user's finger. The target point may be marked by the user in the map, for example made recognizable by a higher contrast due to higher density in a specific area. Automatic segmentation of the target point by the planning controller may also be possible.

The trajectory for the method may be easily determined by selection on a map.

In an embodiment of the method the alignment of the first projector with the medical instrument is fixed and is, for example, (anti-)parallel to a trajectory of the medical instrument.

Then, in the step of ascertaining the alignment, only a position of the positioning aid on the wall of the patient tunnel is ascertained in which the luminous pointer of the first projector is caused to coincide with the positioning aid when the medical instrument is aligned parallel to a trajectory through the entry point and the target point. This is achieved in that a point of intersection of the luminous pointer with the inside of the is ascertained, for example by solving a system of equations with a straight line congruent to the trajectory and a mathematical description of the inner wall of the patient tunnel by a cylinder in the planning controller. The point of intersection is then output.

The determination of the point of intersection is particularly simple if the trajectory is parallel to the direction of projection of the luminous pointer.

In an embodiment of the method the point of intersection is output to the user as a coordinate at an operator interface.

Herein, for example, a visible coordinate system is arranged on the inner wall of the patient tunnel. The coordinate system provides the user to clearly identify a position on the inner wall by the coordinates that are output to identify the point of intersection. The user may then target this position identified by the coordinates as a positioning aid with the illuminated viewfinder and thus achieve the desired alignment of the medical instrument.

In an embodiment of the method the outputting of the point of intersection on the inside of the patient tunnel is a marking by the second projector. The second projector may be aligned by an actuator on instruction from the planning controller such that a projection of the second projector as a positioning aid marks the ascertained coordinates of the point of intersection on the inner wall of the patient tunnel. An image projected by the second projector onto the inner wall may be changed so that it marks the ascertained coordinate. It is also possible for a grid of light spots to be provided on the inner wall by LEDs or glass fibers, wherein the light spot closest to the ascertained point of intersection is activated by the planning controller as a positioning aid.

Active marking of the variable point of intersection makes it easier for the user to find the target point for the luminous pointer and thus to align the instrument.

In another embodiment of the method, it is possible to set the alignment of the first projector relative to the instrument. Herein, in the step of ascertaining the alignment, an alignment of the first projector relative to the medical device is determined under which, on alignment of the medical instrument parallel to a trajectory through the entry point and the target point, the light pointer is aligned with the positioning aid. Since, herein, the alignment of the first projector is no longer parallel to the trajectory and thus dependent on the angle of rotation of the instrument about the trajectory. A sensor, such as, for example, a magnetic field sensor or a gravity sensor in the instrument may detect the angle and set the alignment of the first projector in dependence thereon.

The first luminous pointer may not be rotationally symmetrical and may specify an angular position of the instrument if, as described above, the luminous pointer is aligned with an angular marking of the positioning aid. The alignment of the first projector relative to the instrument is then no longer dependent on a rotation of the instrument.

Due to the degrees of freedom gained by a variable position of the first projector, the positioning aid may be provided in a clearly visible position, thus simplifying alignment for the user.

The above-described properties, features and advantages, and the manner in which they are achieve will become clear and more plainly comprehensible in connection with the following description of embodiments, which will be explained in more detail in connection with the drawings.

DETAILED DESCRIPTION

Figure 1:
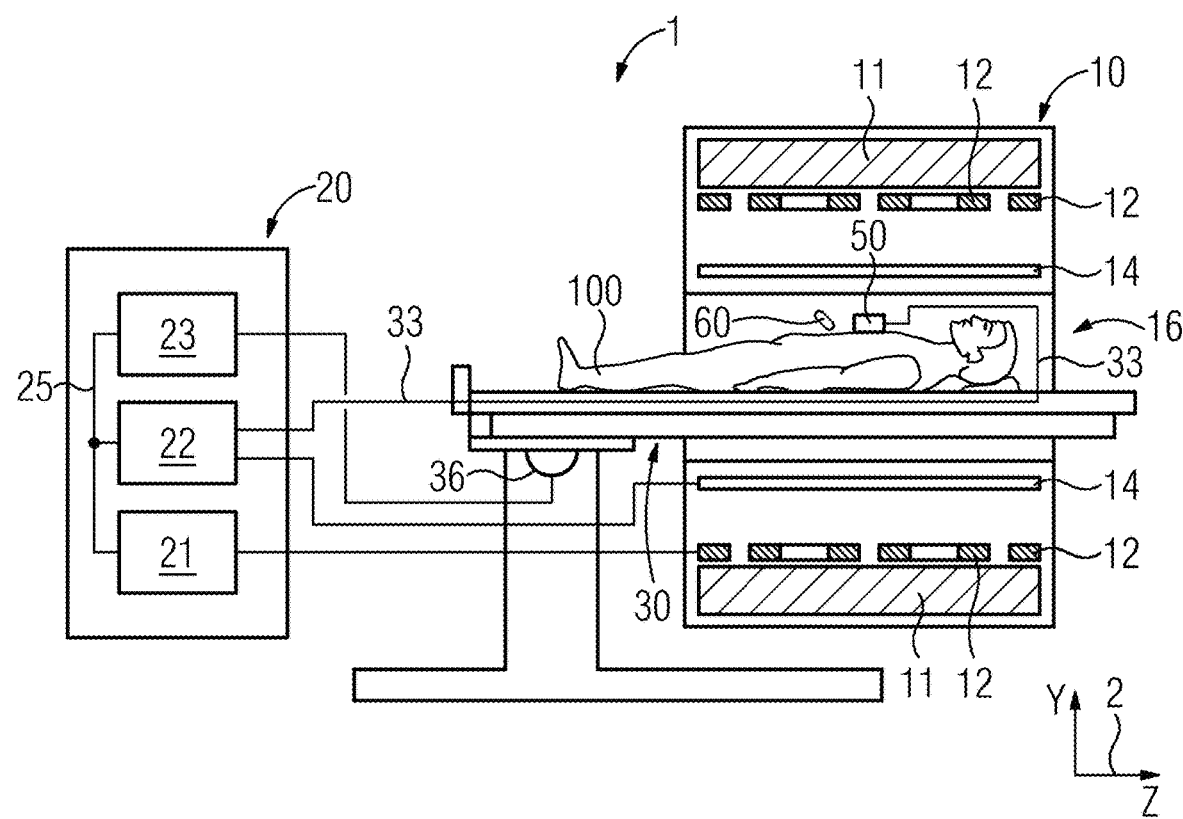
FIG. 1 depicts a schematic representation of a magnetic resonance imaging scanner with an instrument according to an embodiment.

FIG. 1 depicts a schematic representation of an embodiment of a magnetic resonance imaging scanner 1 for executing the method.

The magnet unit 10 includes a field magnet 11 that creates a static magnetic field B0 for aligning nuclear spins of samples or the patient 100 in a recording area. The recording area is characterized by an extremely homogeneous static magnetic field B0. The homogeneity relates to the magnetic field strength or the magnitude.

The recording area is almost spherical and arranged in a patient tunnel 16 that extends in a longitudinal direction 2 through the magnet unit 10. A patient couch 30 may be moved in the patient tunnel 16 by the drive unit 36. The field magnet 11 may be a superconducting magnet able to provide magnetic fields with a magnetic flux density of up to 3T, or even more in the case of the latest devices. However, for lower magnetic field strengths it is also possible to use permanent magnets or electromagnets with normally conducting coils.

The magnet unit 10 furthermore includes gradient coils 12 configured to superimpose temporally and spatially variable magnetic fields in three spatial directions on the magnetic field B0 for spatial differentiation of the acquired mapping regions in the examination volume. The gradient coils 12 may be coils made of normally conducting wires that may create mutually orthogonal fields in the examination volume.

The magnet unit 10 likewise includes a body coil 14 configured to radiate a radio-frequency signal supplied via a signal line 33 into the examination volume and to receive resonance signals emitted by the patient 100 and output them via a signal line 33.

A control unit 20 supplies the magnet unit 10 with the various signals for the gradient coils 12 and the body coil 14 and evaluates the received signals.

Thus, the control unit 20 includes a gradient actuator 21 configured to supply the gradient coils 12 with variable currents via supply lines which provide the desired gradient fields in the examination volume in a time-coordinated manner.

The control unit 20 includes a radio-frequency unit 22 configured to create a radio-frequency pulse with a prespecified temporal course, amplitude and spectral power distribution for exciting a magnetic resonance of the nuclear spins in the patient 100. Herein, pulse powers in the kilowatt range may be achieved. The excitation signals may be radiated into the patient 100 via the body coil 14 or also via a local transmitting antenna 50.

A controller 23 communicates with the gradient controller 21 and the radio-frequency unit 22 via a signal bus 25.

A medical instrument 60, for example a biopsy needle, is arranged on a patient 100 in a patient tunnel 16.

Figure 2:
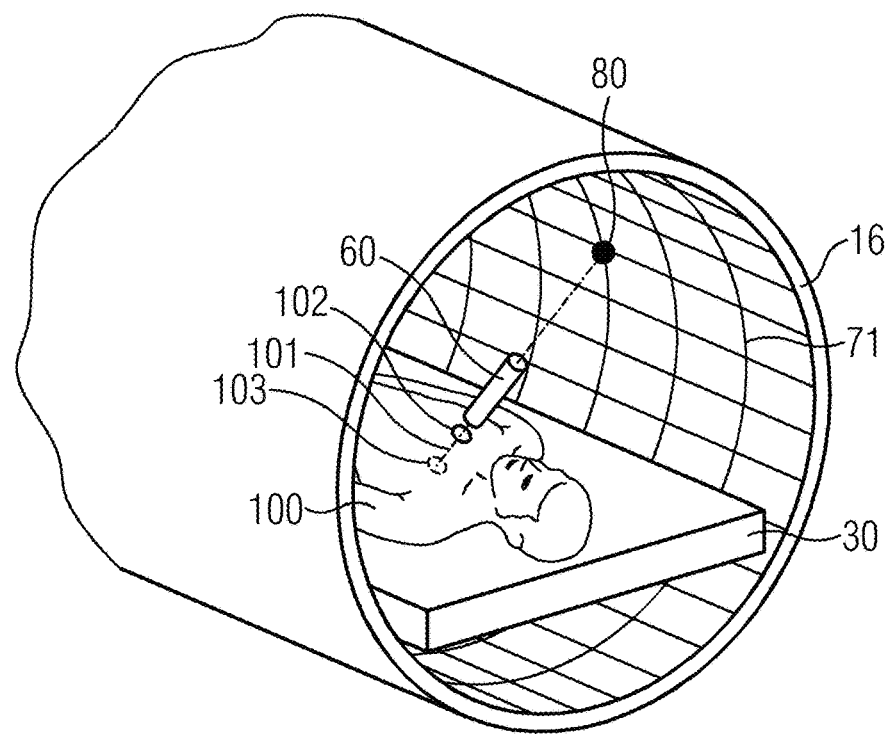
FIG. 2 depicts a schematic representation of an embodiment of a magnetic resonance imaging scanner with an instrument.

FIG. 2 shows a detail of an embodiment in FIG. 1.

There is a predetermined target point 103 in the patient, for example a node, that was identified with its coordinates in a map of the patient 100. A medical instrument 60, for example a biopsy needle, with which a sample is to be taken from the target object at the target point 103 is placed on an entry point on the surface of the patient which is indicated by a marking 102. The marking may also be visible in a magnetic resonance image. However, a marking 102 formed solely by the impression made by the instrument 60 in the patient may also be visible in the magnetic resonance image. A trajectory 101, a straight line, connects the entry point and the target point 103. The trajectory may be selected such that it does not hit any important organ, blood vessel, nerve, or other tissue to be protected.

The predetermined trajectory 101 includes a point of intersection with the patient tunnel 16 or the inner wall thereof on a side facing away from the patient 100. If the relative position of the patient 100 to the magnetic resonance imaging scanner 1 is known, this point of intersection may be calculated using the methods of linear algebra. One possibility for determining the trajectory 101 and point of intersection is provided by a magnetic resonance recording of the patient 100 in which the target object 103 and the planned entry point is visible. The point of intersection calculated by the controller 23, for example, may be output to a user in the form of coordinates for a coordinate system 71 attached to the inner wall in a visible manner. This provides the user to identify the predetermined position 80 on the inner wall of the patient tunnel 16 where the trajectory 101 intersects the inner wall. The user may align the instrument 60 in FIG. 2 parallel to the trajectory 101 and thus to the target object 103 if, as shown in more detail in FIG. 3, this projects a light spot or a luminous pointer 70 and the user causes this luminous pointer 70 to coincide with the predetermined position 80. The coordinate system 71 may be projected onto the inner wall of the patient tunnel 16 by a second projector 90.

Figure 3:
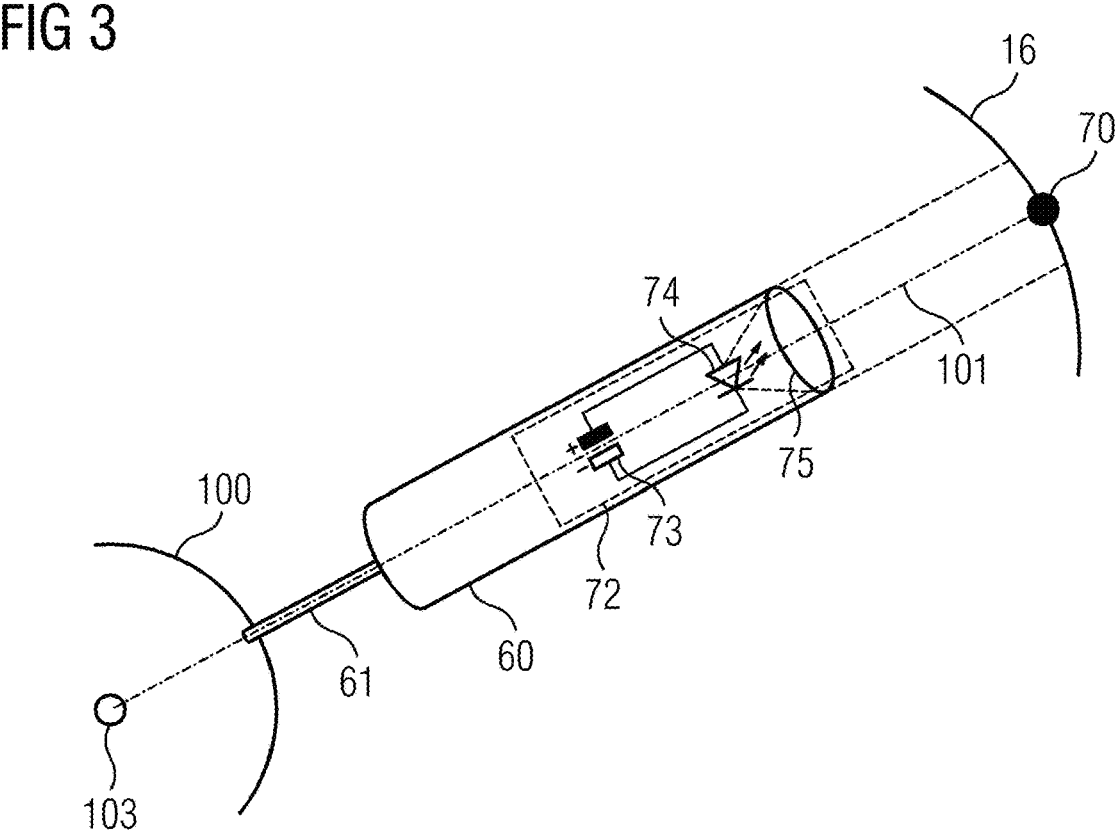
FIG. 3 depicts a schematic representation of an embodiment of an instrument.

FIG. 3 is a schematic representation of an embodiment of the medical instrument. The medical instrument 60 includes an axis of symmetry, defined here by the biopsy needle 61. The symmetry to the axis of symmetry reflects a symmetry of the medical instrument 60 or the application to be performed therewith. In the case of the biopsy needle, this may be rotated about an axis through the longitudinal extent of the hollow needle 61 during the application without further consequences. Accordingly, the axis of symmetry of the medical instrument 60 in FIG. 2 is an axis of rotation through the longitudinal extent of the hollow needle 61. If this is caused to coincide with the predetermined trajectory 101, the alignment of the medical instrument 60 is aligned correctly with the target object 103.

For this purpose, the medical instrument 60 in FIG. 3 includes a first projector 72. The first projector 72 includes a power source, for example a battery 73. However, the power source may also be a power supply line. The power source supplies a light source, for example a semiconductor laser 74. However, other light sources, such as lamps or an OLED matrix may be used. The light created is focused by an optical system 75 into a light beam that is emitted parallel to the axis of symmetry of the medical instrument 60 in a direction opposite to the patient 100. When the light beam strikes a surface, for example the inner wall of the patient tunnel 16, it creates a light pointer 70 there in the form of a dot or spot or a more complex pattern, as detailed below.

If the medical instrument 60 is arranged with the tip or the hollow needle 61 at the entry point and the user aligns the luminous pointer 70 with the predetermined position 80, these two fixed points define a straight line, which corresponds to the predetermined trajectory 101 and ensures alignment of the medical instrument 60 in accordance with the invention.

Figure 4:
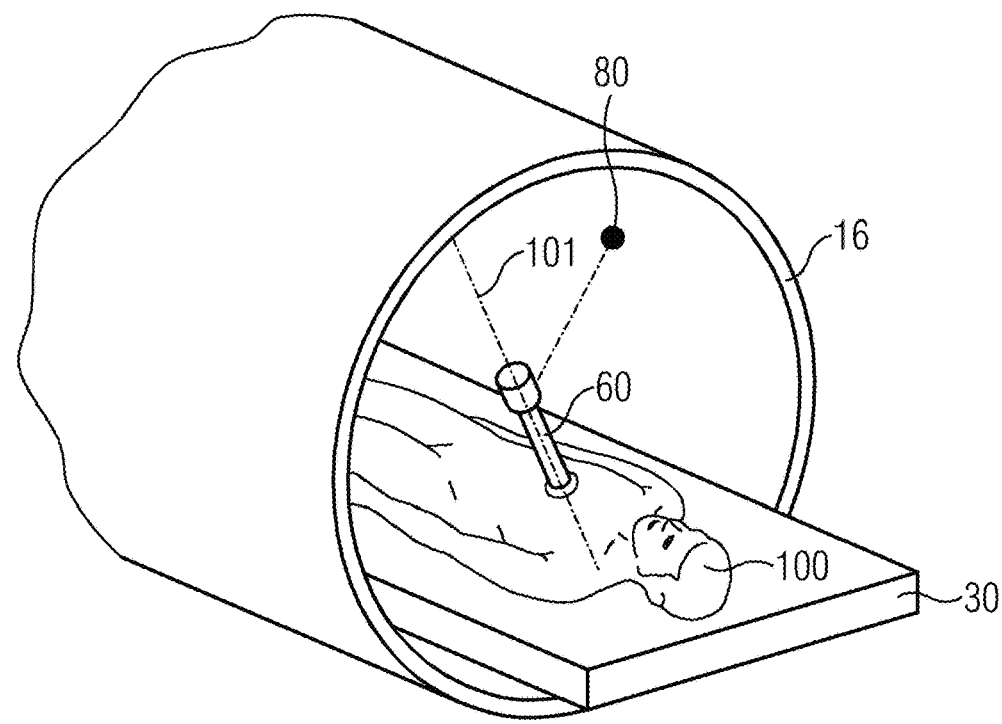
FIG. 4 depicts a schematic representation of an embodiment of a magnetic resonance imaging scanner with an instrument.

FIG. 4 is a representation of an embodiment of the medical instrument 60 and the magnetic resonance imaging scanner 1. The same reference numbers denote the same objects, for example the trajectory 101 is still defined as the straight line through the entry point and target object 103. The embodiment represented in FIG. 4 essentially differs in that the trajectory 101 no longer matches the direction of projection of the luminous pointer 70. This makes it possible to no longer select constantly changing coordinates on the inside of the patient tunnel 16 as the predetermined position 80, but only to mark one or a few predetermined positions 80, which are then, for example, marked by a fixed marking, such as an elevation or depression or reflex point. However, the alignment of the first projector 72 relative to the medical device 60 has to be changed in each case, as represented in detail in FIG. 5.

Figure 5:
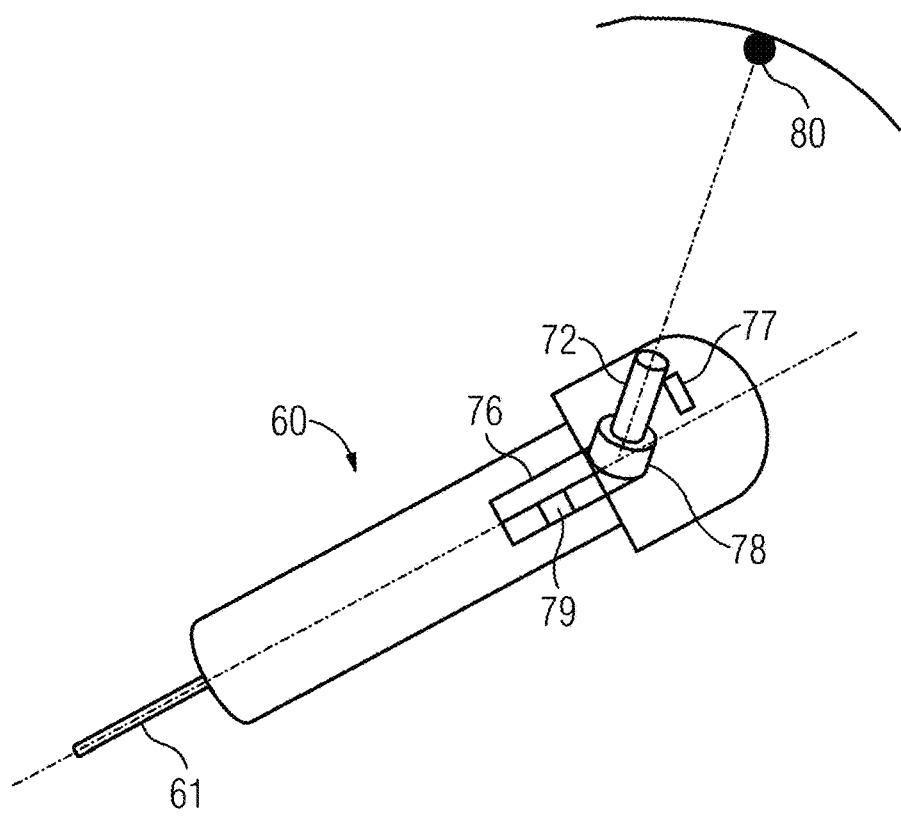
FIG. 5 depicts a schematic representation of an embodiment of an instrument.

In FIG. 5, the first projector 72 is no longer aligned parallel to the axis of symmetry of the medical instrument 60, but may be changed by a first actuator 77 and an optional second actuator 78 relative to the axis of symmetry. For example, a projector controller 76 in the medical instrument may receive setting instructions, for example wirelessly, from the controller 23 of the magnetic resonance imaging scanner 1. The control instructions may specify an angular alignment with respect to the axis of symmetry by the first actuator 77 and/or an angular alignment with respect to a rotation about the axis of symmetry by the second actuator 78. The first actuator and the second actuator may, for example, be motors, for example piezoelectric actuators, that execute a linear movement or a rotation without requiring a disruptive magnetic field.

Herein, the angles to be set depend upon a rotation of the instrument 60 about the axis of symmetry relative to the magnetic resonance imaging scanner or also the direction of gravity. This rotation may be detected by the projector controller 76 by a sensor 79 and transmitted to the controller 23 for ascertaining the angles for the first actuator 77 and the second actuator 78. The sensor 79 may, for example, be a MEMS-based gravity sensor or a multi-dimensional Hall sensor.

The first projector 72 may be configured as freely rotatable about the axis of rotation and the weight distribution may be set such that the first projector 72 has a preferred direction under the effect of gravity, for example directed upward against the force of gravity.

Figure 6:
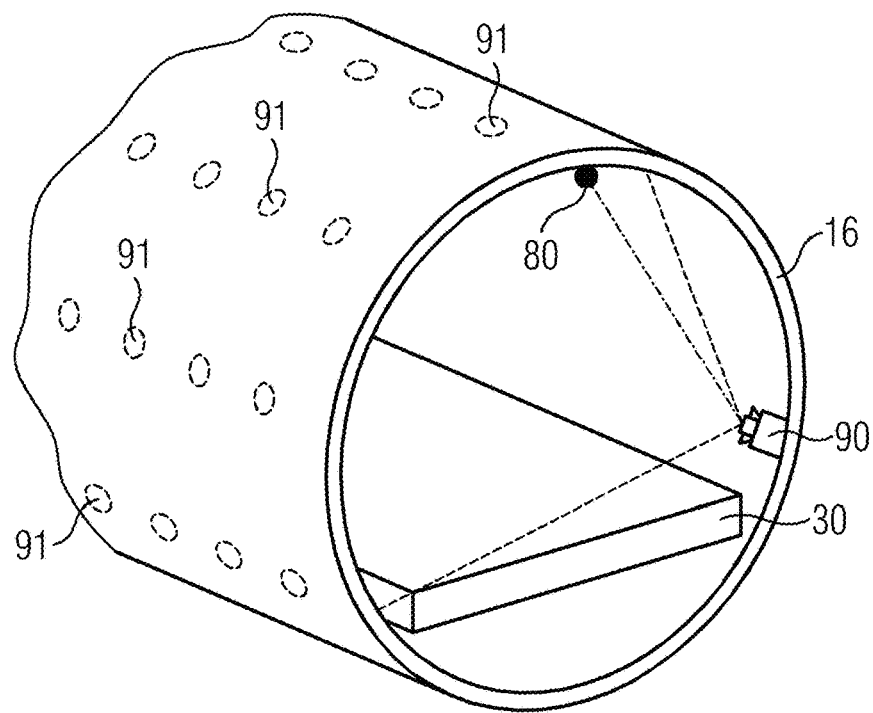
FIG. 6 depicts a schematic representation of an embodiment of a magnetic resonance imaging scanner.

FIG. 6 is a representation of two possibilities for marking the predetermined position 80 in a magnetic resonance imaging scanner 1.

A second projector 90 is attached in or on the patient tunnel 16 and projects into the interior thereof. The second projector 90 may, for example, project an image with a variable position and/or alignment as a predetermined position 80 for the luminous pointer 70. The image may, for example, be created with an OLED, LCD or DLP matrix. The second projector 90 may be variably aligned using actuators, as was explained in FIG. 5 with respect to the first projector 72.

However, a variable marking of the predetermined position 80 may also be created, for example by a switchable matrix of light spots 91 on the inner wall of the patient tunnel 16, which are, for example, created by LEDs and optionally transmitted by light guides to the inner wall of the patient tunnel 16.

Figure 7:
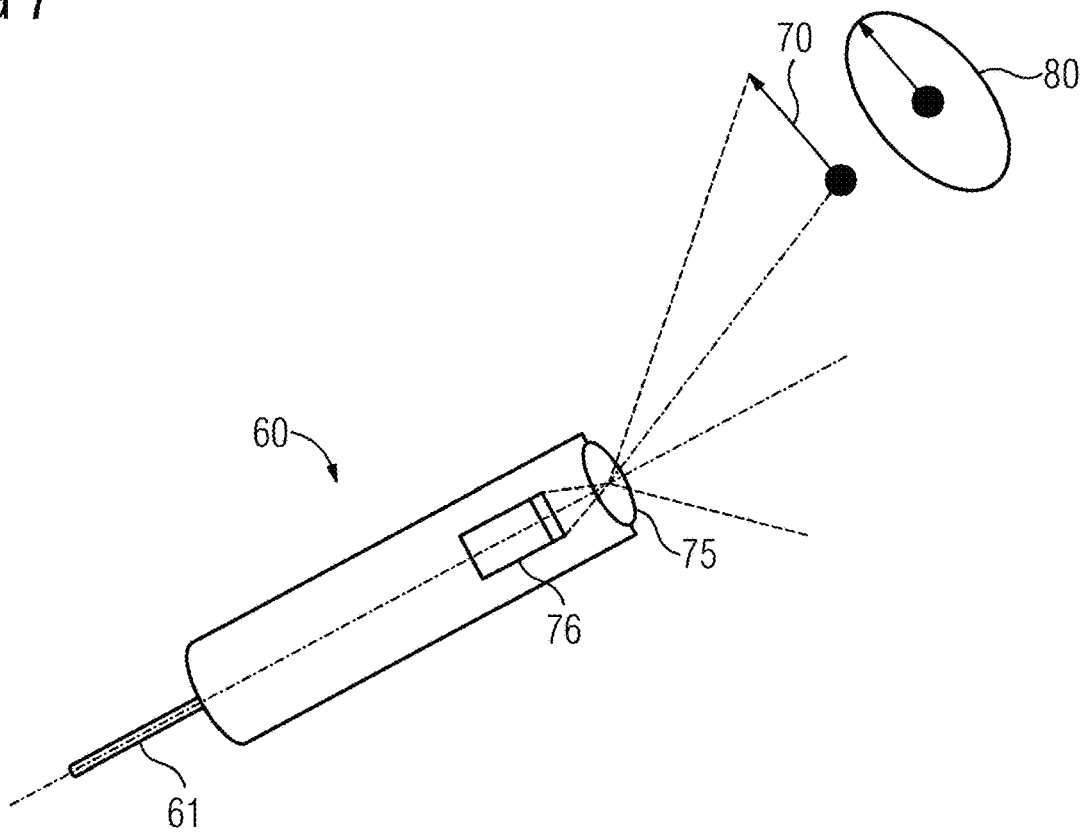
FIG. 7 depicts a schematic representation of an embodiment of an instrument.

FIG. 7 is a schematic representation of an embodiment of a medical instrument 60. The embodiment represented represents an alternative to the variant represented in FIG. 5. Instead of aligning the first projector 72 differently by a first actuator 77 and/or second actuator 78, the projected image is changed. The first projector 72 includes a projection angle that is, for example, greater than 20 degrees, 40 degrees or 60 degrees. This may cause the luminous pointer 70 to coincide with the predetermined position 80 in many different alignments of the trajectory 101. The luminous pointer 70 marks a position and a direction, for example by the point of origin and the alignment of the arrow in FIG. 7. Causing this luminous pointer 70 to coincide with a predetermined position 80, likewise marked by a location marking and a direction marking, may also achieve a defined position of the medical instrument 60 for rotation about the axis of symmetry.

Figure 8:
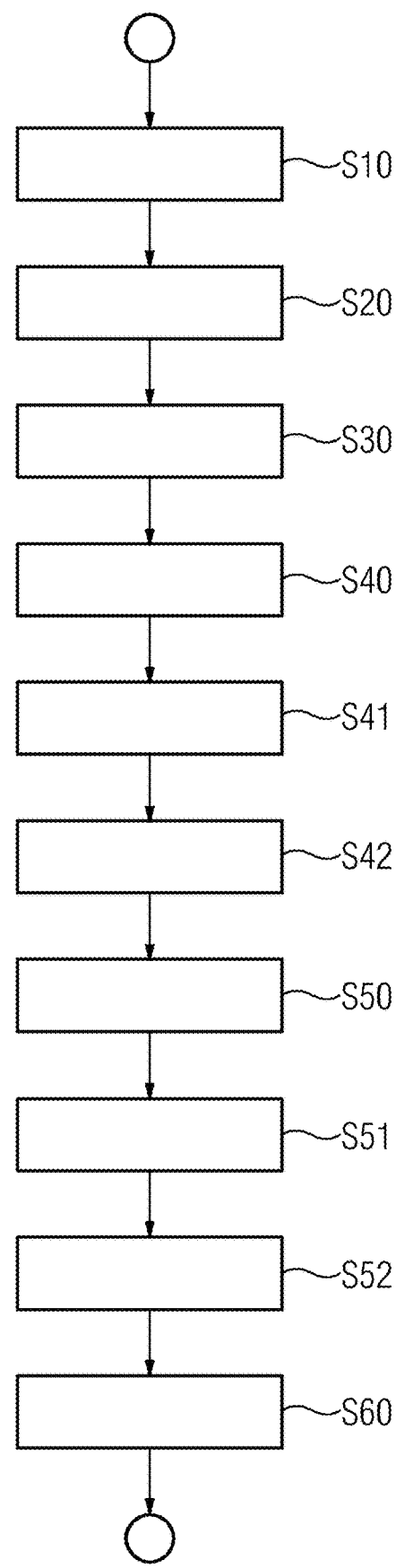
FIG. 8 depicts a schematic flow diagram of a method according to an embodiment.

FIG. 8 depicts a schematic flow diagram of a method.

In a step S30, the patient 100 is positioned in the magnetic resonance imaging scanner 1, for example with the patient table 30. The patient 100 is to undergo a minimally invasive examination or an intervention by a medical instrument 60 on an organ or tissue, that is referred to below as the target object 103. The way in which this entry point may be determined is explained below. Herein, the positioning takes place such that the entry point and the target object 103 are located in a detection area of the magnetic resonance imaging scanner 1, that is also referred to as the field of view (FoV). The correct position may, for example, be verified using markings 102 on the patient 100 and magnetic resonance imaging scanner 1 or fast image acquisition using the magnetic resonance imaging scanner 1. At the end of the positioning, the patient 100 is in a known relative position and alignment relative to the magnetic resonance imaging scanner 1.

In another step S40 of the method a predetermined alignment of the first projector 72 relative to the medical instrument 60 and/or position of the positioning aid on the wall of the patient tunnel 16 is ascertained in which the luminous pointer 70 of the first projector 72 coincides with the positioning aid when the medical instrument is aligned parallel to a trajectory 101 through the entry point and the target point.

Step S40 differs for cases in which the first projector 72 is aligned parallel to the axis of symmetry of the medical instrument, as in FIG. 3, or may itself be aligned with the axis of symmetry, as in FIG. 5 or FIG. 7.

For the embodiment in FIG. 3 with an axis of symmetry parallel to the trajectory 101, a point of intersection of the trajectory through the predetermined entry point and target object 103 with the inner wall of the patient tunnel 16 on a side of the instrument 60 facing away from the patient 100 is determined in a step S41. This may, for example, take place by solving a system of equations in which the straight-line equation of the trajectory 101 is equated with an envelope of the inner wall.

In the embodiments in FIGS. 5 and 7, an alignment of the first projector 72 may be set at an angle relative to the axis of symmetry of the medical instrument 60 and an angle of rotation about the axis of symmetry. The predetermined position 80 may be arranged in an invariable manner on the inner wall of the patient tunnel 16 and marked graphically or by a structure. In this case, the alignment of the first projector 72 is determined in a step S42 such that the luminous pointer 70 of the first projector falls onto the predetermined position 80 when the medical instrument 60 is aligned parallel to the trajectory 101 in a manner appropriate for the application. This may be done by solving a system of equations in which the trajectory 101 is multiplied by a rotation matrix containing as variables the two angles of alignment of the first projector 72 and that is equated with the predetermined position 80. The solution according to the two angles provides the alignment of the first projector 72 to be determined, for example by the controller 23 of the magnetic resonance imaging scanner 1. during the ascertaining, the projector controller 76 may ascertain, by a sensor 79, a position of the medical instrument 60 relative to the magnetic resonance imaging scanner 1 and the alignment is ascertained in dependence on this position. For example, this position may be included as an offset in the angle of rotation.

In a step S50, the result of the ascertaining in step S40 is output.

For an embodiment of the medical instrument 60 with fixed parallel alignment of the first projector 72 and the luminous pointer 70 created thereby with the axis of symmetry, the coordinate for the predetermined position 80 may be output in a step S51 on an output of the magnetic resonance imaging scanner 1. A second projector 90 may indicate the predetermined position 90 in that the second projector 90 is aligned by actuators with the predetermined position 80 by the controller 23. The second projector 90 may be aligned in a fixed manner, but outputs a variable image with a settable position of a projected marking for the predetermined position 80 which is, for example, set by the controller 23.

For an embodiment in which the first projector 72, or at least the luminous pointer 80 projected thereby, is variable in alignment relative to the medical instrument 60, the outputting takes place in a step S52, for example in that the first actuator 77 and second actuator 78 are aligned accordingly by a setting instruction from the controller 23 to the projector controller 76.

In an embodiment with a fixed first projector 72 that projects an image, the projector controller 76 sets the image such that the luminous pointer 70 is projected in the ascertained alignment relative to the medical instrument 60.

The luminous pointer 70 is then projected by the first projector 72.

In another step S60, the medical instrument 60 is positioned at the predetermined entry point. This may be done by a user and may also be done earlier in the method.

Finally, in a step S60, the medical instrument is aligned such that the luminous pointer 70 is caused to coincide with the positioning aid. This may be done by the user by tilting, swiveling and/or rotating the medical instrument 60 until the light pointer 70 coincides with the predetermined position 80. The tip of the medical instrument 60 remains at the entry point. In an embodiment in which the light pointer 70 and the marking for the predetermined position 80 includes a direction marking for displaying directional information, the alignment of the medical instrument 60 may also include rotating the medical instrument 60 about the axis of symmetry until the direction markings coincide.

In an embodiment, the method furthermore includes the step S10 of outputting a map of the patient 100 on the operator interface of the planning controller. The planning controller may be identical to the controller 23 of the magnetic resonance imaging scanner 1. The map contains at least the target object 103 and an area around a possible entry point. The map may be a magnetic resonance scan with the magnetic resonance imaging scanner 1. The map may be acquired with another modality and may be provided on a data carrier or via a data network connection.

In a further step S20, an entry point is defined on the surface of the patient and a target point is defined in the target area 103 in the patient 100. The target point may be defined by an organ or tissue identifiable in the map, for example a node or an entire organ. The entry point may already be marked in the map by a marker detected by the modality. The entry point may only be defined based on the map, for example with the requirement that no sensitive tissue is damaged on the way from the entry point to the target area.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for positioning a medical instrument on a patient with a magnetic resonance imaging scanner that includes a positioning aid configured to mark a predetermined position on an inner wall of a patient tunnel in a manner that is visible to a user, the medical instrument comprising a first projector configured for projecting a luminous pointer in a predetermined alignment relative to the medical instrument, the method comprising:
    positioning the patient in the magnetic resonance imaging scanner such that a predetermined entry point for the medical instrument on a surface of the patient and a predetermined target point of an intervention in the patient are located in a detection area of the magnetic resonance imaging scanner;
    ascertaining a predetermined alignment of the first projector relative to the medical instrument in which the luminous pointer of the first projector coincides with the positioning aid when the medical instrument is aligned parallel to a trajectory through the entry point and the target point or ascertaining a position of the positioning aid on the wall of the patient tunnel, in which the luminous pointer of the first projector coincides with the positioning aid when the medical instrument is aligned parallel to the trajectory through the entry point and the target point;
    aligning the first projector or outputting coordinates that relate to a coordinate system that is attached to the inside wall of the patient tunnel in a visible manner to the user; and
    projecting the luminous pointer.

2. The method of claim 1, wherein the method further comprises:
    aligning the medical instrument such that the luminous pointer coincides with the positioning aid.

3. The method of claim 1, wherein the method further comprises:
    providing a map of the patient on an operator interface of a planning controller; and
    defining an entry point on the surface of the patient and a target point in the patient.

4. The method of claim 1, wherein an alignment of the first projector with the medical instrument is fixed and parallel to an axis of symmetry of the medical instrument, and wherein a point of intersection of the luminous pointer is determined and the point of intersection is output.

5. The method of claim 1, wherein an alignment of the first projector with the medical instrument is set by the magnetic resonance imaging scanner, and for ascertaining the alignment, an alignment of the first projector relative to the medical instrument is determined under which, on alignment of the medical instrument parallel to a trajectory through the entry point and the target point, the luminous pointer is aligned with the positioning aid, and the first projector is aligned according to the determined alignment.

\* \* \* \* \*